United States Patent [19]

Faust et al.

[11] 4,035,484

[45] July 12, 1977

[54] CALCIUM HYPOCHLORITE COMPOSITIONS

[75] Inventors: John P. Faust, Hamden; Henry R. Cramer, Naugatuck, both of Conn.

[73] Assignee: Olin Corporation, New Haven, Conn.

[21] Appl. No.: 669,419

[22] Filed: Mar. 22, 1976

[51] Int. Cl.$^2$ .................... C09K 3/00; C01B 11/06; C02B 3/06
[52] U.S. Cl. ................ 424/149; 423/265; 423/474; 252/187 H
[58] Field of Search ............... 252/187 H; 423/265, 423/474; 424/14, 149; 260/557 H

[56] References Cited

U.S. PATENT DOCUMENTS

| | | | |
|---|---|---|---|
| 2,121,501 | 6/1938 | Hershman | 424/149 |
| 3,296,069 | 1/1967 | Kowalski | 424/14 |
| 3,342,674 | 9/1967 | Kowalski | 252/187 H |
| 3,793,216 | 2/1974 | Dychdala et al. | 252/187 H |

*Primary Examiner*—Oscar R. Vertiz
*Assistant Examiner*—Brian E. Hearn
*Attorney, Agent, or Firm*—James B. Haglind; Donald F. Clements; Thomas P. O'Day

[57] ABSTRACT

Novel compositions comprising calcium hypochlorite and a hydrazide of a monocarboxylic acid containing from about 10 to about 24 carbon atoms have been produced. The compositions provide accurately controlled concentrations of available chlorine to bodies of water such as swimming pools by reducing the solubility of the calcium hypochlorite.

8 Claims, No Drawings

CALCIUM HYPOCHLORITE COMPOSITIONS

This invention relates to calcium hypochlorite compositions. More particularly, this invention relates to calcium hypochlorite compositions having decreased solubility in water.

Calcium hypochlorite is a well known source of available chlorine for disinfecting and sanitizing water supplies such as swimming pool water. As a source of available chlorine, the calcium hypochlorite is a highly soluble material which dissolves rapidly in water. For example, at 30° C. about 21.6 grams of granular calcium hypochlorite dissolves in 100 grams of water with all of the calcium hypochlorite dissolving in less than 5 minutes. Thus, solutions of available chlorine can be provided rapidly by the direct addition of calcium hypochlorite to the water.

Where, however, dilute solutions of available chlorine are desired by directly adding the calcium hypochlorite to the water supply, its normally favorable solubility properties require periodic additions of the material to a water supply such as a swimming pool, which may be considered an inconvenience, for example, by a swimming pool operator.

It is therefore desirable to provide a calcium hypochlorite composition having reduced solubility in water which will provide the carefully controlled release of small concentrations of available chlorine continuously and for an extended period of time when added directly to the water supply.

It is known in the prior art to use active chlorine compounds such as calcium hypochlorite in mixtures containing as a binding agent a metal salt of a carboxylic acid having at least 10 carbon atoms, for example, sodium stearate; along with calcium oxide and sodium carbonate. As described in German Offenlegungschrift 1,959,708, issued to T. E. Schneider, Jr. et al, cylinders of these mixtures are employed in the sanitation and disinfection of water. These mixtures are also available in tablet form.

Also known are tablets containing calcium carbonate, a complex mixture of fatty acids and minor amounts of fatty acid amides, where the fatty acid components contain from about 16 to about 22 carbon atoms. These tablets are sold by TESCO Corporation under the trade name Hy-Clor 66.

There is a need for calcium hypochlorite compositions which extend the time for dissolution beyond that of the above materials while providing a composition having improved processability and intermixing properties. It is therefore an object of the present invention to provide novel calcium hypochlorite compositions for sanitizing water supplies.

A further object of the present invention is to provide novel calcium hypochlorite compositions having reduced solubility for sanitizing water supplies.

These and other objects of the invention will be apparent from the following description of the invention.

It has now been discovered that the aforesaid objects are accomplished by employing a coherent solid composition comprising calcium hypochlorite and a hydrazide of a monocarboxylic acid containing from about 10 to about 24 carbon atoms.

More in detail, hydrazides which can be used in the novel compositions of the present invention include the monohydrazides of aliphatic monocarboxylic acids containing from about 10 to about 24 carbon atoms. Suitable hydrazides include decanoic acid hydrazide, 2-tetradecanoic acid hydrazide, lauric acid hydrazide, myristic acid hydrazide, palmitic acid hydrazide, stearic acid hydrazide, elaidic acid hydrazide, eicosanoic acid hydrazide, docosanoic acid hydrazide and tetracosanoic acid hydrazide and mixtures thereof. Preferred monohydrazides are those of aliphatic monocarboxylic acids containing from about 12 to about 20 carbon atoms. Illustrative of these hydrazides are lauric acid hydrazide, 2-tetradecanoic acid hydrazide, myristic acid hydrazide, palmitic acid hydrazide, stearic acid hydrazide, elaidic acid hydrazide, and eicosanoic acid hydrazide.

Anhydrous calcium hypochlorite has been available commercially for a number of years. Recently "hydrated" calcium hypochlorite having a water content of from about 4 to about 15 percent has been introduced. Hydrated calcium hypochlorite may be prepared by the methods described, for example, in U.S. Pat. No. 3,544,276, issued to G. R. Dychdala or U.S. Pat. No. 3,669,894, issued to J. P. Faust. Anhydrous and hydrated calcium hypochlorite in granular form are both quite suitable in preparing the novel compositions of the present invention. The calcium hypochlorite content of these products is from about 50 to about 80, and preferably from about 60 to about 75 percent by weight of $Ca(OCl)_2$. Calcium hypochlorite having greater or lesser amounts of $Ca(OCl)_2$ may be used if desired. Granular calcium hypochlorite normally has a particle size range of from about 10 to about 200 mesh U.S. Standard Screen.

The novel coherent solid compositions comprising calcium hypochlorite and a monocarboxylic acid hydrazide may contain any suitable proportion of the hydrazide compound which is effective in reducing the solubility of the calcium hypochlorite. For example, a proportion of monocarboxylic acid hydrazide of from about 0.01 to about 10.0, and preferably from about 0.5 to about 3.0 percent by weight of the calcium hypochlorite.

The coherent solid compositions of the present invention may be prepared by any of several well known methods including, for example, the direct mixing of the components followed by tabletting, pelletizing or compacting or by applying a coating of the hydrazide compound to particles of calcium hypochlorite, for example, by spray graining. It is preferred that the coherent solid compositions be of a homogeneous mixture of the calcium hypochlorite and the hydrazide compound. Suitable product forms include tablets, pellets, briquettes or stick forms, with tablets or pellets being preferred forms.

Calcium hypochlorite is widely used as a disinfectant and sanitizing agent for supplying available chlorine in the treatment of water supplies such as swimming pool water. To sanitize swimming pool water, available chlorine concentration ranging from less than 1 part per million to a few parts per million are continually maintained. In conventional methods of application, granular calcium hypochlorite is periodically added directly to the water in the pool in quantities sufficient to maintain the available chlorine at or above the desired levels. It is preferred, however, to provide continuous contact between the pool water and the solid calcium hypochlorite. Placing tablets of the coherent solid calcium hypochlorite composition of the present invention in the skimmer or in dissolving baskets around the pool is a suitable method of accomplishing this. Another method is to add solid calcium hypochlorite to a dispensing device in which the calcium hypochlorite is contacted with the water to be treated to form a concentrated solution of available chlorine.

Many devices have been developed to control the dissolution of solid compounds containing available chlorine components such as calcium hypochlorite. Typical examples include those of U.S. Pat. Nos. 2,700,651; 2,738,323; 3,495,948; 3,598,536; 3,607,103; 3,615,244; 3,638,833; 3,727,632; 3,802,845; 3,806,394; 3,864,090; and 3,807,471. In each of these devices the contact between the water and the readily soluble solid calcium hypochlorite is controlled either by metering the amount of calcium hypochlorite added to the stream of water or by limiting the degree of contact of the water with the calcium hypochlorite.

The coherent solid calcium hypochlorite compositions of the present invention have been found to significantly reduce the solubility of the calcium hypochlorite. The calcium hypochlorite and the hydrazide compound readily intermix to facilitate formulation of the coherent compositions. When contacted with water, the compositions dissolve at a constant rate to provide a carefully controlled release of small concentrations of available chlorine.

The novel compositions of the present invention can also be employed in the sanitizing of water in urinals, latrines or toilets or in the treatment of water in cooling towers.

The following examples are presented to further illustrate the invention without any intention of being limited thereby. All parts and percentages are by weight unless otherwise specified.

EXAMPLE 1

A homogeneous mixture containing 99 percent by weight of commercial calcium hypochlorite [70 percent by weight of $Ca(OCl)_2$] and 1 percent by weight of stearic hydrazide was prepared. A three inch diameter tablet having a weight of about 195 grams was formed by pressing the mixture at a load of 20–25 tons. The tablet was placed in a floating feeder basket which floated in a reservoir containing 100 liters of water. Water was circulated by a pumping system through the reservoir to simulate the circulation system of a swimming pool. In addition to visually observing the dissolving of the tablet, a sample of water was removed from the reservoir periodically and the available chlorine concentration determined to provide an indication of the degree of dissolution of the tablet. The results are reported in Table I.

EXAMPLE 2

The dissolving procedure of Example 1 was used with a tablet 3 inches in diameter weighing about 195 grams produced from a mixture containing 98.5 percent by weight of commercial calcium hypochlorite [70.4 percent by weight of $Ca(OCl)_2$] and 1.5 percent by weight stearic hydrazide. Results are reported in Table I.

COMPARATIVE TEST A

The procedure of Example 1 was repeated with a tablet containing 100 percent by weight of commercial calcium hypochlorite (70.4 percent by weight of $Ca(OCl)_2$). The results are reported in Table 1.

COMPARATIVE TESTS B AND C

The procedure of Example 1 was employed for producing and dissolving tablets 3 inches in diameter, weighing about 195 grams, and containing 99 percent by weight of calcium hypochlorite [70.4 percent by weight of $Ca(OCl)_2$] and 1 percent by weight of sodium stearate, (Test B) and 98.5 percent by weight of calcium hypochlorite [70.4 percent by weight of $Ca(OCl)_2$] and 1.5 percent by weight of sodium stearate (Test C). See Table I for the results of these tests.

COMPARATIVE TEST D

The procedure of Example 1 was employed to dissolve a commercially available tablet (TESCO HY-CLOR 66) 3 inches in diameter, weighing 203 grams, and containing 64.4 percent by weight of calcium hypochlorite. The tablet also contains calcium carbonate and a complex mixture consisting of fatty acids and a minor amount of fatty acid amides; the fatty acids having from about 16 to about 22 carbon atoms and molecular weights up to 632, as identified by infrared and mass spectroscopy analysis. Results of the dissolution are given in Table I.

| DISSOLVING TIME FOR CALCIUM HYPOCHLORITE COMPOSITION TABLETS | | | | |
|---|---|---|---|---|
| (Tablets: 3 inches in diameter, weight 195–203 grams) | | | | |
| Example No. | $Ca(OCl)_2$ % by weight | Additive | Additive % by weight | Total Dissolving Time (in hours) |
| 1 | 99 | Stearic hydrazide | 1 | 156 |
| 2 | 98.5 | Stearic hydrazide | 1.5 | 211 |
| Comparative Test | | | | |
| A | 100 | none | | 8 |
| B | 99 | Sodium stearate | 1.0 | 125 |
| C | 98.5 | Sodium stearate | 1.5 | 145 |
| D | | Fatty acids and fatty amides having 16–22 carbon atoms (mixture) + $CaCO_3$ | 1.0 | 126 |

Table 1 shows the time required to dissolve tablets containing calcium hypochlorite and stearic hydrazide is greatly increaased over that required for mixtures of calcium hypochlorite and sodium stearate or the Tesco Hy-Clor 66 tablet. With tablets containing 1 percent by weight of stearic hydrazide, the increase in time required for dissolution 24.8 percent above that for 1.0 percent by weight of sodium stearate or the mixture in the Tesco tablet; using 1.5 percent stearic hydrazide, the increase is 45.5 percent over that for an equal weight of sodium stearate.

EXAMPLE 3

A tablet weighing 30 grams was prepared from a mixture containing 97.5 percent commercial calcium hypochlorite [66 percent by weight of Ca(OCL)$_2$] and 2.5 percent by weight of stearic hydrazide was dissolved in water, with 76 hours being required for complete dissolution. An identical tablet, containing only the commercial calcium hypochlorite was dissolved in only 5 hours.

What is claimed is:

1. A coherent solid composition comprising calcium hypochlorite and a hydrazide of a monocarboxylic acid containing from about 10 to about 24 carbon atoms.

2. The coherent solid composition of claim 1 in which the proportion of said hydrazide is from about 0.01 to about 10 percent by weight of said calcium hypochlorite.

3. The coherent solid composition of claim 1 in which said monocarboxylic acid contains from about 12 to about 20 carbon atoms.

4. The coherent solid composition of claim 3 in which said proportion of said hydrazide is from about 0.5 to about 3.0 percent by weight of said calcium hypochlorite.

5. The coherent solid composition of claim 4 in which said hydrazide is stearic acid hydrazide.

6. The coherent solid composition of claim 1 in which the form is a pellet or tablet.

7. The coherent solid composition of claim 5 in which said form is a tablet.

8. The coherent solid composition of claim 1 in which said calcium hypochlorite contains from about 50 to about 80 percent by weight of Ca(OCl)$_2$.

* * * * *